United States Patent
Dietz et al.

(10) Patent No.: US 11,744,512 B2
(45) Date of Patent: Sep. 5, 2023

(54) MULTIBEND SHAPE SENSOR

(71) Applicant: Tactual Labs Co., New York, NY (US)

(72) Inventors: Paul Henry Dietz, Redmond, WA (US); Fereshteh Shahmiri, Redmond, WA (US)

(73) Assignee: Tactual Labs Co., New York, NY (US)

( * ) Notice: Subject to any disclaimer, the term of this patent is extended or adjusted under 35 U.S.C. 154(b) by 394 days.

(21) Appl. No.: 17/026,252

(22) Filed: Sep. 20, 2020

(65) Prior Publication Data

US 2021/0137418 A1 May 13, 2021

Related U.S. Application Data

(63) Continuation-in-part of application No. 16/995,727, filed on Aug. 17, 2020, and a continuation-in-part of application No. 16/270,805, filed on Feb. 8, 2019, now Pat. No. 11,221,202.

(60) Provisional application No. 62/903,272, filed on Sep. 20, 2019, provisional application No. 62/887,324, filed on Aug. 15, 2019, provisional application No. 62/748,984, filed on Oct. 22, 2018.

(51) Int. Cl.
| | |
|---|---|
| *A61B 5/11* | (2006.01) |
| *G01B 7/28* | (2006.01) |
| *A61B 5/00* | (2006.01) |
| *G01D 5/241* | (2006.01) |

(52) U.S. Cl.
CPC .......... *A61B 5/4566* (2013.01); *A61B 5/1116* (2013.01); *A61B 5/1126* (2013.01); *G01B 7/28* (2013.01); *A61B 2562/164* (2013.01); *G01D 5/2412* (2013.01)

(58) Field of Classification Search
CPC . G01B 7/28; G01B 11/16; G01B 7/20; G01B 7/24; G01B 7/287; G01B 7/22; G01D 5/268; G01D 5/241; G01D 5/16; G01D 3/08; G06F 3/014; A61B 5/1071; A61B 5/6826; A61B 2562/043; A61B 2562/125; A61B 2562/164; A61B 2562/0209
See application file for complete search history.

(56) References Cited

U.S. PATENT DOCUMENTS

| | | | |
|---|---|---|---|
| 8,931,351 B2 * | 1/2015 | Muramatsu | G01D 5/16 73/849 |
| 2009/0151478 A1 * | 6/2009 | Shimomoto | G01L 1/146 73/862.626 |
| 2009/0293631 A1 * | 12/2009 | Radivojevic | G01L 1/16 73/774 |

(Continued)

*Primary Examiner* — Christopher P McAndrew
*Assistant Examiner* — Zannatul Ferdous
(74) *Attorney, Agent, or Firm* — Adam Landa

(57) ABSTRACT

A multibend sensor comprises a reference strip having a first plurality of electrodes, wherein each of the first plurality of electrodes is adapted to receive a signal; a sliding strip having a second plurality of electrodes, wherein each of the second plurality of electrodes is adapted to transmit at least one signal, wherein the sliding strip moves with respect to the reference strip; and measurement circuitry adapted to process signals received by the first plurality of electrodes, wherein the processed signals provide information regarding the relative position of the sliding strip to the reference strip.

16 Claims, 10 Drawing Sheets

(56) References Cited

U.S. PATENT DOCUMENTS

| | | | |
|---|---|---|---|
| 2011/0018557 A1* | 1/2011 | Badaye | G06F 3/0446 |
| | | | 324/658 |
| 2011/0182458 A1* | 7/2011 | Rosener | G06V 40/1306 |
| | | | 381/384 |
| 2013/0133435 A1* | 5/2013 | Muramatsu | G01B 7/18 |
| | | | 73/799 |
| 2016/0253031 A1* | 9/2016 | Cotton | G06F 3/0445 |
| | | | 345/174 |
| 2016/0254328 A1* | 9/2016 | Song | H01L 51/525 |
| | | | 324/699 |
| 2017/0265810 A1* | 9/2017 | Van De Vyver | A61B 5/1126 |
| 2018/0113003 A1* | 4/2018 | Huang | G01B 7/20 |

* cited by examiner

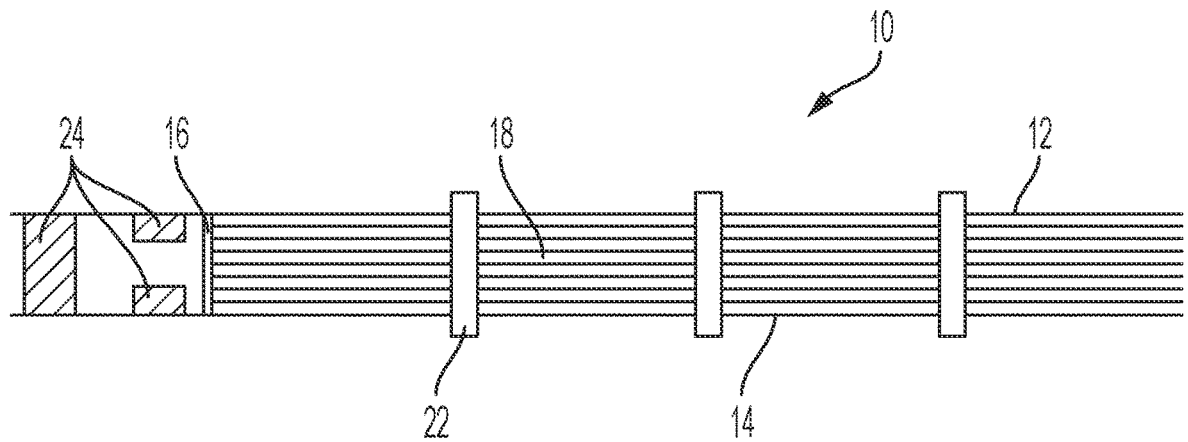
FIG. 1
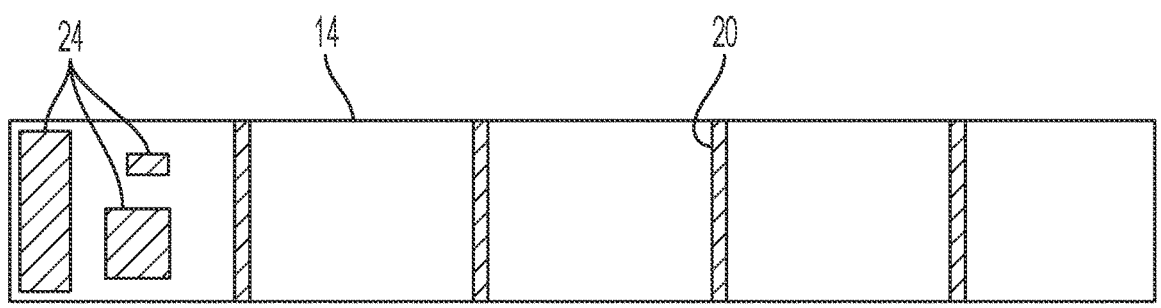
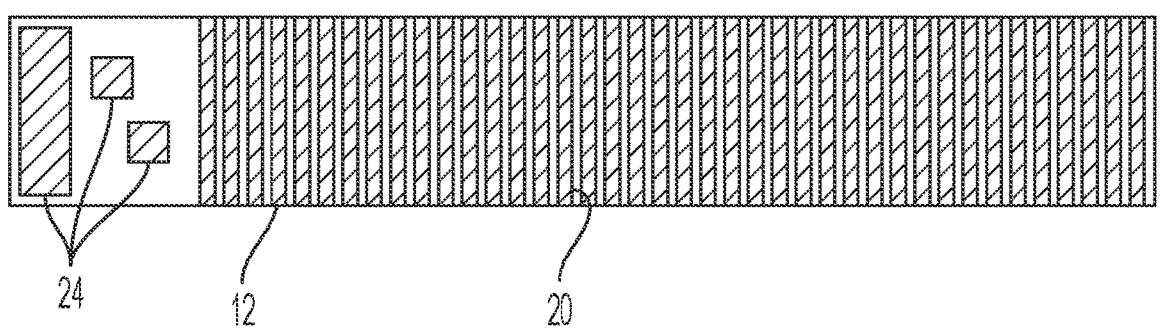
FIG. 2

MULTIBEND SHAPE SENSOR

This application claims the benefit of U.S. Provisional Application No. 62/903,272 filed Sep. 20, 2019; which claims the benefit of U.S. Provisional Application No. 62/887,324 filed Aug. 15, 2019. This application is a continuation in part of U.S. patent application Ser. No. 16/270,805 filed Feb. 8, 2019, which claims the benefit of U.S. Patent Provisional Application No. 62/748,984 filed Oct. 22, 2018. The contents of all of the aforementioned applications are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed apparatus and methods relate to the field of sensing, and in particular to providing accurate determination of positioning using a multibend sensor.

BACKGROUND

In the past, sensing gloves have been employed to detect hand gestures. An example is the Dataglove, set forth in U.S. Pat. No. 5,097,252, which employed optical bend sensors along the fingers to detect finger position. Nintendo's Power Glove used a similar design, but with resistive bend sensors. In both cases, the bend sensors were not very sensitive, providing only a single measure of the overall bend for each bend sensor.

Bend sensors are used in applications beyond finger and hand sensing. They are often employed to understand human motion more generally. Recent decades have seen tremendous progress in the development of high accuracy sensors and their low cost, mass production. Much of this has been driven by smartphones which include an impressive array of sensors. Despite these advancements, there are still many things about the physical world that have proven surprisingly difficult to sense with an inexpensive, precision device. We consider the challenging problem of sensing the shape of a dynamically deforming object.

The desire to understand shape arises in many applications. In robotics, rotary joints are frequently cascaded to allow dexterous, multi-axis motion that must be monitored to be actively controlled. Launching a large rocket has been compared to "pushing on a string", and it requires a detailed understanding of dynamic flexure. Bridges, storage tanks, planes many other structures are subject to repeated load cycling and understanding deformation in these systems can help prevent catastrophe. More germane to the Human-Computer Interaction (HCI) community, our bodies are quite flexible. In medicine and sports performance, it is often important to understand the range and type of motion. Motion capture is critically important to both the gaming and movie industries. In virtual and augmented reality, a real-time understanding of detailed hand pose allows compelling interactions. For performance, musicians and other artists can manipulate shape intuitively to provide expressive control of key systems.

To better understand the positions of systems with multiple joints, some systems have used a bend sensor per joint, or at each point of articulation. There are challenges with this approach that limit its practicality. For example, the bend sensors have to be custom fitted for the spacing between joints. The need for fitting for the spacing can be problematic for tracking human motion because of size variation in people.

Additionally, there is the problem of cascaded error from the joint measurements. For example, the angle of each successive segment of a finger may be determined as the sum of the joint angles to that segment. Thus, any errors in the angle measurements taken for each of the preceding joints accumulate. Therefore robot arms use extremely high precision angular encoders to find a modestly precise position. Unfortunately, inexpensive bend sensors have poor angular precision making them inadequate for understanding the impacts of cascaded joint error.

Systems have attempted to overcome this shortcoming by using cameras and other sensing techniques to directly measure finger positions. Camera-based techniques are challenged by the difficulty of finding good viewpoints from which to view what is happening. Other position sensor systems can be bulky and/or expensive. Inertial tracking can be used but it has severe drift issues.

There are also Fiber Bragg Grating sensors that permit measuring bends along the length of a fiber bundle and can recover detailed shapes of a particular geometry. These sensors are difficult to make and require significant, bulky instrumentation and complex calibration. Further, they are expensive and impractical for most applications.

Most of the prior work uses sensors that give a single measure of bend. To sense complex curves, one can employ a series of single bend sensors, building a model of connected joints. This works best when the underlying thing to be sensed is well modelled as a series of linkages. However, placement of the sensors requires an a priori understanding of the joint locations. For example, when modelling human joints such as a finger, there is significant variation in location from person to person, precluding a general solution.

Complex curves may require a large number of single bend sensors to provide an adequate understanding of shape. Unfortunately, each additional bend sensor contributes measurement error, which accumulates to progressively degrade the overall accuracy of the system. This severely limits the maximum number of single bend sensors that can reasonably be employed.

Recently, machine learning approaches have been applied to understanding the output of systems with many single bend sensors. While these systems have the potential to combine the readings from large numbers of single bend sensors such that error does not accumulate in such a direct fashion, they require extensive training. It is also unclear if any reduction in accumulated error comes from imposing constraints that make the system less general The most common way of detecting flexure is by measuring the changing properties of a material under strain. Spectra Symbols' Flex sensor is an example. Strain is a problematic proxy for flexure. Stretching, environmental conditions, and other factors can induce strain that cannot be easily distinguished from that due to bending. Continual strain cycles can also cause material fatigue.

The most common strain-based bend sensors are resistive, optical including Fiber Bragg Grating (FBG) sensors, piezoelectric or capacitive. We consider each of these and discuss their operation. Resistive bend sensors are similar to resistive strain gauges but are optimized for much larger bends. A layer of resistive material is placed on a flexible substrate and undergoes strain as the sensor is bent. A bend away from the side with the resistive material causes tensile strain, increasing the resistance.

Resistive sensors suffer from significant drift due to fatigue, aging of materials and environmental conditions, and require constant recalibration to achieve even modest accuracy. Because they provide only a single measure of bend, they cannot distinguish shape for complex curves. For example, in the case of monitoring finger bend, the sensor cannot distinguish flexure at different joints from one another. Although resistive bend sensors have many limitations, they are quite inexpensive and easy to interface to, allowing use in many applications. The best known of these is the Nintendo PowerGlove, an early consumer hand pose interface device used for gaming. have embedded commercial flex sensors into both soft and rigid materials to create different control interactions like switches or sliders. Ink jet printing has been used to form customized shapes to create game controllers and toys in two and three dimensions.

Fiber Optic Shape Sensors (FOSS) are comprised of flexible tubes with reflective interior walls which have a light transmitter and receiver at opposite ends. FOSS recover the bend shape by measuring changes in intensity, phase, polarization or wavelength of the light while the flexible tube is bent.

Fiber Bragg Grating (FBG) sensors employ an optical fiber that has been processed to create a grating that interacts with light of a specific wavelength. As the fiber is bent, the grating is mechanically expanded or compressed, which shifts the wavelength of interest. Generally, a tunable laser is used to scan for the new wavelength of the deformed grating. Different wavelength grating patterns can be placed at different locations along the fiber, allowing the degree of bending to be independently measured at each location.

FOSS can be extremely thin and light weight with little restriction on the length of the sensor. They are relatively precise and immune to electromagnetic inferences. While these sensors can provide impressive performance, it comes at a very high price. A tunable laser interrogator may cost as much as USD$10,000—a cost that severely limits the practical applications. While the fiber can be quite thin, the interrogators tend to be large and power hungry. They require complex fabrication process and calibration as well as sophisticated signal processing. They have restricted range of measurement for curvatures and fall into non-linearity very quickly. These reasons limit their use cases to very specific applications like medical devices but not for daily human routines.

Piezoelectric bend sensors are based on deformation and strain in piezo materials. Such deformations change the surface charge density of the material and cause charge transfer between the electrodes. The amplitude and frequency of the signal is directly proportional to the applied mechanical stress. Piezoelectric sensors, similar to triboelectric sensors, suffer from drift and only provide signal while in motion. This limits their application to dynamic bending only and not static or low-frequency deformations.

Most resistive strain sensors have high-latency and are unable to measure the absolute angles of bend. The hysteresis properties of conductive materials produce varying conductivity during cyclic loading. Most resistive and FBG (Fiber Bragg Grating) sensors are non-linear in response to large strains.

An alternative to strain sensing is what we call geometric sensing. These sensors much more directly measure curvature by sensing geometric changes that are a result of bending. Examples include, measuring relative displacements of different sensor layers.

Therefore, there is a need for an improved method and apparatus for accurately determining bending through the use of sensors and to improve the accuracy of such bending.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

FIG. 1 shows a side view of a multibend sensor.

FIG. 2 shows a bottom up view of a sensor strip.

DETAILED DESCRIPTION

Figure 3:
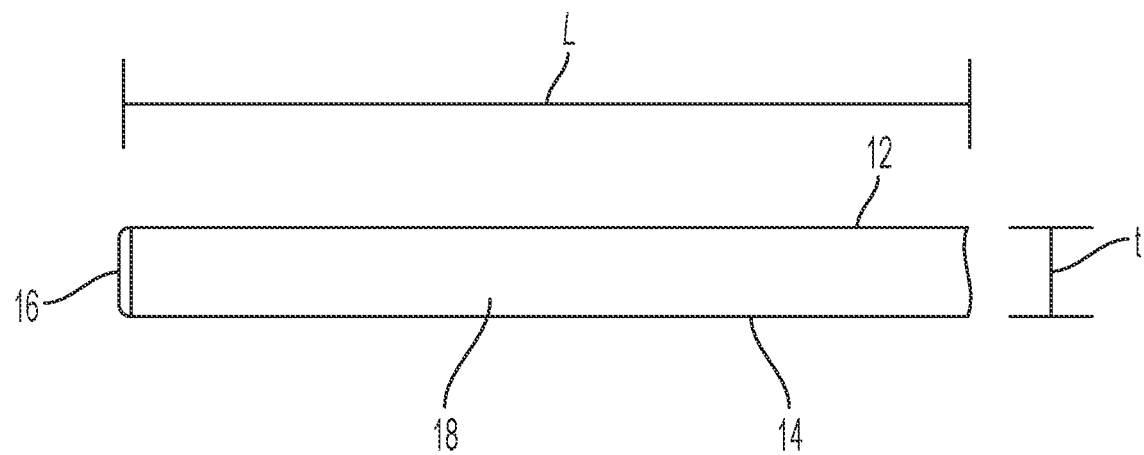
FIG. 3 is a schematic view of sliding and reference sensor strip.

The present application describes various embodiments of multibend sensors and methods for making such sensors. Embodiments and techniques described herein allow for the accurate measurement of complex curves. In an embodiment, a multibend sensor detects multiple bends. In an embodiment, a multibend sensor measures over many points.

In an embodiment, a multibend sensor is a capacitive sensor. As will be noted by those skilled in the art, capacitive bend sensors work either by material strain or displacement between sensor layers. Either way the geometric changes vary the effective overlapping surface areas for capacitive coupling and/or the spacing between conductors as a function of the bending angle. Capacitive sensors can be more linear than other techniques. They are inexpensive to produce and more stable than resistive sensors.

In an embodiment, a multibend sensor is a low cost, precise, dynamic sensor for sensing bends and reconstructing the detailed shape of curves. In an embodiment, a multibend sensor comprises a stack of flexible strips that can be formed into complex curves in a plane. In an embodiment, a multibend sensor measures curvature by noting the relative shift between inner and outer layers of the sensor at many points.

In an embodiment, a multibend sensor measures the relative shift two strips to measure complex curves. In an embodiment, a multibend sensor comprises at least two flexible strips that can be dynamically formed into complex curves in a plane. In an embodiment, a multibend sensor comprises a plurality of transmitting and receiving electrode segments. In an embodiment, the measurement error on one segment causes a compensating error the other direction on the next segment. Embodiments described show advantageous qualities over joint encoding for curves with significant complexity. In an embodiment, a multibend sensor measures local curvature by noting the relative shift between the inner and outer layers of the sensor at many points and models the shape as a series of connected arcs. In an embodiment, techniques are provided to sense the shape of a dynamically deforming.

Referring now to FIGS. 1 and 2, shown is an embodiment of a multibend sensor 10. FIG. 1 shows a schematic side view of the multibend sensor 10. In the embodiment shown, the multibend sensor 10 has a sliding strip 12 and a reference strip 14. FIG. 2 shows a top view of the reference strip 14 and a bottom view of the sliding strip 12. The sliding strip 12 is secured to the reference strip 14 at a distal end 16 of the reference strip 14. In the embodiment shown there is a spacer 18 located between the sliding strip 12 and the reference strip 18. In an embodiment, a multibend sensor 10 has multiple spacers 18. Additionally, shown are retainers 22 that retain the sliding strip 12 and the reference strip 14 against the spacer 18. In an embodiment, a multibend sensor 10 comprises a plurality of flexible strips that are joined together at one end. In an embodiment, the sliding strip 12 and the reference strip 14 are separated by at least one spacer 18 and wherein the sliding strip 12 and the reference strip 14 are held at a constant distance apart via an elastic sleeve which compresses them against the at least one spacer 18.

Operably connected to the sliding strip 12 and the reference strip 14 is circuitry 24 that is adapted to receive and process measurements that occur. In the embodiment shown, the circuitry 24 may comprise components, or be operably connected to components, such as processors, signal generators, receivers, connectors, etc.

The sliding strip 12 and the reference strip 14 may be formed from flexible printed circuit board strips. While the sliding strip 12 and the reference strip 14 are shown having specific electrode patterns, it should be understood that the roles of each of the respective strips may be changed and that the sliding strip 12 may function as the reference strip 14 and vice versa depending on the particular implementation. Electrodes 20 may be placed on the surfaces of the sliding strip 12 and the reference strip 14. The electrodes 20 are adapted to transmit and receive signals. The electrodes 20 may be arranged in any pattern that is capable of determining a change during the bending of the sliding strips 12 and the reference strip 14. Additionally, the number, size and shape of the electrodes 20 implemented on sliding strip 12 and the reference strip 14 may be changed based on a particular implementation. In an embodiment, the circuitry 24 is operably connected to the electrodes 20. The circuitry 24 processes the signals received from the electrodes 20 to measure the relative shift between the electrodes in the different strips as the strips are formed into curves.

Still referring to FIGS. 1 and 2, the sliding strip 12 and the reference strip 14 are flexible and able to move and bend. Additionally, the spacer 18, which is placed between the sliding strip 12 and the reference strip 14, is flexible and able to move and bend. In an embodiment, the spacer 18 may have different levels of flexibility with respect to the sliding strip 12 and the reference strip 14. In an embodiment, the sliding strip 12, the reference strip 14 and the spacer 18 may each have different levels of flexibility. In an embodiment, there is no spacer 18 and the sliding strip 12 and the reference strip 14 move with respect to each other.

The spacer 18 used in the embodiments preferably keeps the strips spaced at a constant distance regardless of the amount of bending, yet still permits relative sliding. Spacer 18 preferably has a thickness that is able to permit there to be differences between the lengths of the sliding strip 12 and the reference strip 14 when there is bending. In an embodiment, there may be no spacer and the sliding strip 12 and the reference strip 14 may be abutting each other, however there should still be sufficient distance between the outward facing sides to permits sensing of the relative shift between the sliding strip 12 and the reference strip 14 during a bend. In an embodiment, the spacer 18 may have the same flexibility as the sliding strip 12 and the reference strip 14. A thick spacer 18 will provide a good amount of shift, but the spacer 18 itself may change thickness with a tight bend. A thin spacer 18 will have this issue less but may not provide adequate shifting. In an embodiment, the spacer 18 may be made out of a series of thin layers which slide against each other. This allows a thick spacer 18 to have fairly tight bends without changing overall thickness.

Having a known spacing between the reference layer and sliding layers assists in obtaining accurate data. Ensuring the spacing can be accomplished by different methods. As discussed above with respect to FIG. 1, retainers 22 can be affixed to one strip and provide compressive force to the other strip that slides against it as shown. The retainers 22 may be plastic or elastic pieces that provide a compressive force to the reference strip 14 and the sliding strip 12. The compressive force should be such that it maintains the distance but does not inhibit movement of the reference strip 14 and the sliding strip 12. In an embodiment, elastomeric sleeves can be used to achieve the same task, providing compressive force.

At the end portion 16, the sliding strip 12 and the reference strip 14 are secured together. In an embodiment, the sliding strip 12 and the reference strip 14 are mechanically attached together. In an embodiment, the sliding strip 12 and the reference strip 14 are integrally secured to each together. In an embodiment, the sliding strip 12 and the reference strip 14 are secured at a location other than the distal end. In an embodiment, the sliding strip 12 and the reference strip 14 are secured in the middle of the strip. Elsewhere along the lengths of the sliding strip 12 and the reference strip 14, the sliding strip 12 and the reference strip 14 slide with respect to each other. The sliding strip 12 and the reference strip 14 also slide against the spacer 18 relative to each other. The retainers 22 ensure that the sliding strip 12 and the reference strip 14 remain pressed against the spacer 18 so as to keep a constant distance between them. Circuitry 24 and electrical connections between the strips are outside of the sensing area where the bending occurs. In the embodiment shown in FIGS. 1 and 2, the circuitry 24 is located proximate to end portion 16 where the sliding strip 12 and the reference strip 14 are joined. The sliding strip 12 and the reference strips 14 contain patterns of electrodes 20 that will allow the electronics to detect the relative shift between the two strips at many locations by measuring the coupling from electrodes 20 on the sliding strip 12 and the electrodes 20 on the reference strip 14 through the spacer 18.

The embodiment discussed above may be made using the materials and techniques implemented to create flexible circuits. Flexible circuits may start with a flexible, insulating substrate such as polyimide. A thin conducting layer (such as copper, silver, gold, carbon, or some other suitably conducting material) is adhered to the substrate with an adhesive. In an embodiment, the conducting layer is patterned using photolithographic techniques. In an embodiment, the conducting layer is applied by sputtering. In an embodiment, the conducting layer is applied by printing. When applied via printing, conductive ink can be directly patterned onto the substrate.

Similar to rigid printed circuit boards (PCBs), flexible circuits can be manufactured to include multiple conductive layers, separated by insulators. Vias may provide connections among the different layers. Like rigid PCBs, standard electrical components may be affixed to flexible circuits using soldering and other well-known techniques. However, because some components are not flexible, flexing their attachments may lead to broken electrical connections. For this reason, flexible circuits may employ stiffeners in the area of components, so that the region of the circuit does not appreciably flex. For similar reasons, flexible circuits tend not to place vias in regions that are actually bending since the stresses in those areas may sometimes lead to breakage.

Many electrode patterns for the multibend sensor can benefit from the use of interlayer connections in bending regions. Dupont® has developed special conductive inks that are explicitly designed to withstand repeated flexure. However other suitable flexible conductive inks may be used as well. These inks can be implemented in the multibend sensors discussed herein. Flexible inks permit flexible connections between conductive layers, serving the role of vias. It should be noted that these flexible conductive inks are compatible with a wide range of substrates, including fabric. This allows for the construction of multibend sensors that are directly integrated into clothing. Additionally, in an embodiment clothing is made from fibers that function as multibend sensors. When implementing multibend sensor fibers stiffeners may be added in order to restrict the movement of the multibend sensor fibers.

Figure 5:
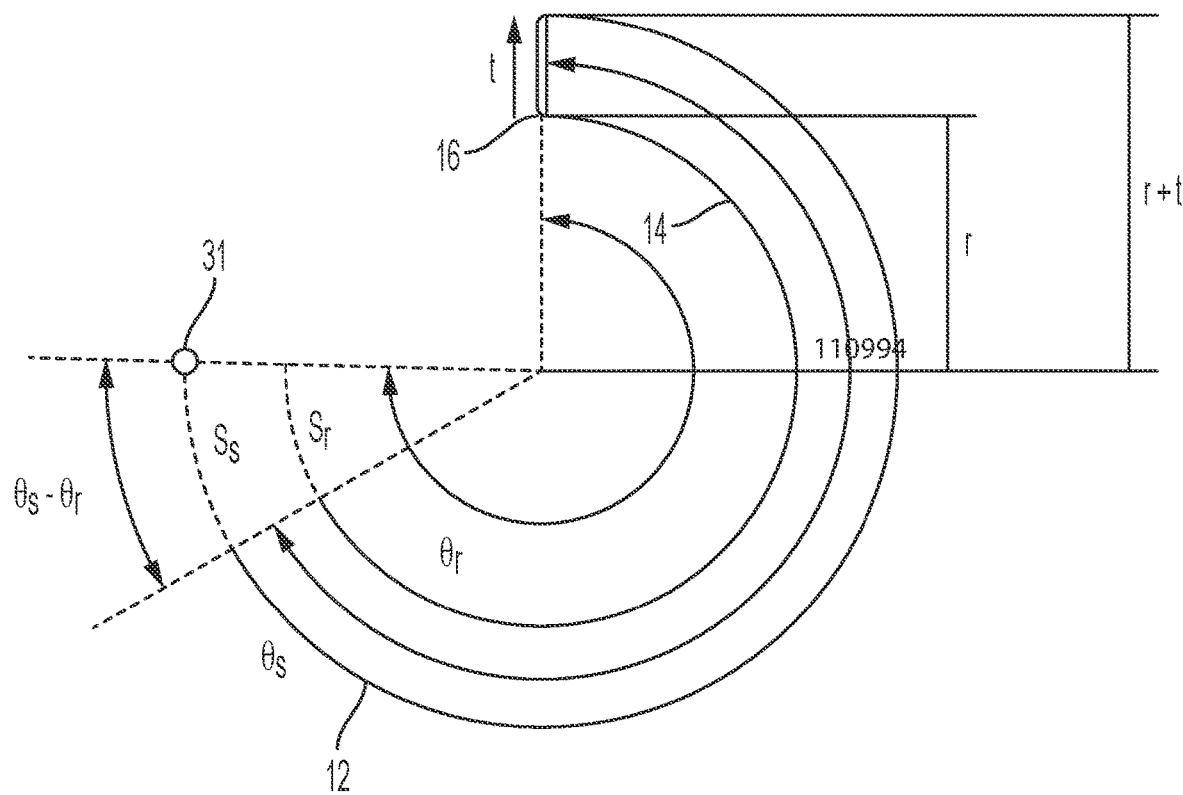
FIG. 5 is a diagram illustrating a sliding strip wrapped around a spacer.

In the following discussion, a multibend sensor comprising a sliding strip and a reference strip may be analogized to a pair of measuring tapes of length L, separated by a spacer of thickness t as shown in as shown in FIG. 3. Similar to the binding of a book, in an embodiment, the strips are joined together on one end. In an embodiment, when the strips are in a flat orientation, the imaginary distance markings of the measuring types perfectly align. However, if the pair is formed around a cylinder of radius r, the inner tape measure will be formed into a circular arc of radius r, while the outer tape measure will be formed into a circular arc of radius r+t (as shown in FIG. 5 and discussed in more detail below). Because they are conjoined on one end, the zero markings of the two tape measures will still align, but the other markings will get progressively misaligned. This is because it takes more tape to subtend the same angle on a larger radius. In an embodiment, when a multibend sensor is formed around a circular arc, the radius r can be calculated knowing only the spacing and the relative shift between the tape measures. In an embodiment, relative shift can similarly be measured at many points along the sensor, each allowing us to measure the curvature of successive segments. In this way, we can measure complex curves that are well modelled as a series of circular arcs.

Figure 4:
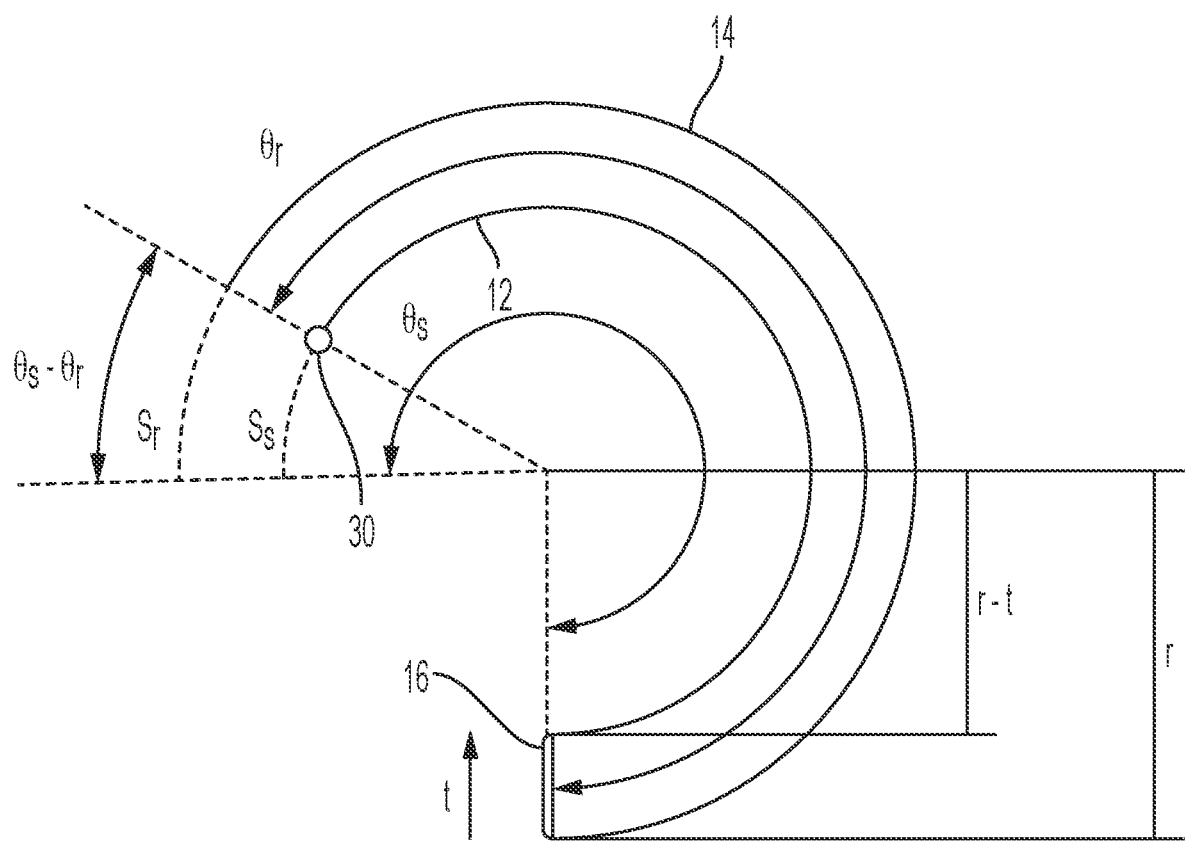
FIG. 4 is a diagram illustrating a reference strip wrapped around a spacer.

Referring now to FIGS. 3-5, when the multibend sensor is wrapped around an object in a circle, the inner of the two strips conforms to the circle, while the outer strip conforms to a slightly larger circle due to the thickness of the spacer 18.

Because the two strips have different radii of curvature, the unconstrained ends will not align with each other. By knowing the length of the strips, sliding strip 12 and reference strip 14 and the thickness of the spacer 18, the radii can directly be calculated. If the relative shift between the two strips at many places is measured a model of the bend as a series of circular arcs can be constructed. This provides a much better understanding of the shape of the bend as opposed to traditional sensors.

Still referring to FIGS. 3-5, to illustrate the way in which the multibend sensor works, take two strips of length L, the sliding strip 12 and the reference strip 14 separated by a spacer 18 of thickness t. The sliding strip 12 and the reference strip 14 are joined together at end point 16 and cannot move relative to one another at that end. When the reference strip 14 is wrapped into a circle of radius r as shown in FIG. 4, the reference strip 14 will have a radius of curvature of r, while the sliding strip 12 will have a smaller radius of r−t.

The circumference of the circle is 2πr. The reference strip 14, which is of length L, covers a fraction of the circle:

$$\frac{L}{2\pi r}$$

To put it in terms of radians, the angle subtended by this strip is:

$$\theta_r = \frac{L}{r}$$

As shown in the diagram, when curled in the direction of the thickness measurement t, the sliding strip 12 ends up on the inside, with a smaller radius of curvature. The tighter wrap means that some of the sliding strip 12 extends beyond the end of the reference strip 14. If this continues along a circle of the same radius, the sliding strip 12 subtends an angle of:

$$\theta_s = \frac{L}{r-t}$$

The end of the reference strip 14 lines up with a corresponding point 30 on the inner sliding strip 12. To give a more precise definition, it is the intersection point on the sliding strip 12 to the normal constructed through the endpoint of the reference strip 14.

This point can be found on the sliding strip 12 by finding the difference in the angular extent of the two arcs, finding the extending length $s_s$ and subtracting this from the total length L.

$$\theta_r - \theta_s = \frac{L}{r} - \frac{L}{(r-t)} = \frac{Lt}{r(r-t)}$$

The length of the segment $s_s$ of the sliding strip 12 that extends past the sliding strip 12 can be found by dividing the angular extent in radians by $2\pi$ to find the fraction of the circle and multiplying by the circumference.

$$s_s = \frac{Lt}{r(r-t)} \frac{1}{2\pi} 2\pi (r-t) = L\frac{t}{r}$$

Solving these equations for the radius r gives:

$$r = t\frac{L}{s_s}$$

By measuring the relative shift between the strips, the radius of curvature across the length can be calculated using this simple equation.

Now consider the case where bending occurs in a clockwise direction as shown in FIG. 5.

The analysis proceeds much as before, but now the sliding strip 12 is on the outside, with a radius of curvature of r+t.

$$\theta_r = \frac{L}{r}$$

$$\theta_s = \frac{L}{r+t}$$

As before, the goal is to locate the corresponding point 31 on the sliding strip 12 that corresponds to the endpoint of the reference strip 14. However, because the sliding strip 12 is on the outside and thus subtends a smaller angle the arc has to be continued to find the intersecting point. $s_s$ is calculated by finding the angle subtended and the corresponding length on the sliding strip 12.

$$\theta_r - \theta_s = \frac{L}{r} - \frac{L}{(r+t)} = \frac{Lt}{r(r+t)}$$

$$s_s = \frac{Lt}{r(r+t)} \frac{1}{2\pi} 2\pi(r+t) = L\frac{t}{r}$$

This is the same result as obtained in the counterclockwise case. The difference here is that $s_s$ in the first case is the amount the sliding strip 12 extended past the reference strip 14, and in this case, it is the amount extra that would be needed to reach the end of the reference strip 14.

To combine these two cases, consider the radius of curvature to be a signed quantity, with a positive r indicating an arc which proceeds in a counterclockwise direction and a negative r indicating a clockwise direction.

A new variable, $L_s$ is defined as the total length along the sliding strip 12 to line up with the end of the reference strip 14. The signed radius of curvature is:

$$r = t\frac{L}{L - L_s}$$

In FIG. 4, $L_s$<L, gave a positive radius of curvature. In FIG. 5, $L_s$>L, gives a negative radius of curvature. The signed radius of curvature is then used to find the signed angular extent of the reference strip.

$$\theta_r = \frac{L}{r} = \frac{L - L_s}{t}$$

In the following, all angles and radii of curvature are signed.

Reconstructing the Curve from Shift Measurements

In an embodiment, the multibend sensor models shape as a series of circular arcs of different radii to allow for complex curves. By measuring the relative shift at many points along the strips, the curvature of each segment can be quickly determined.

Figure 6:
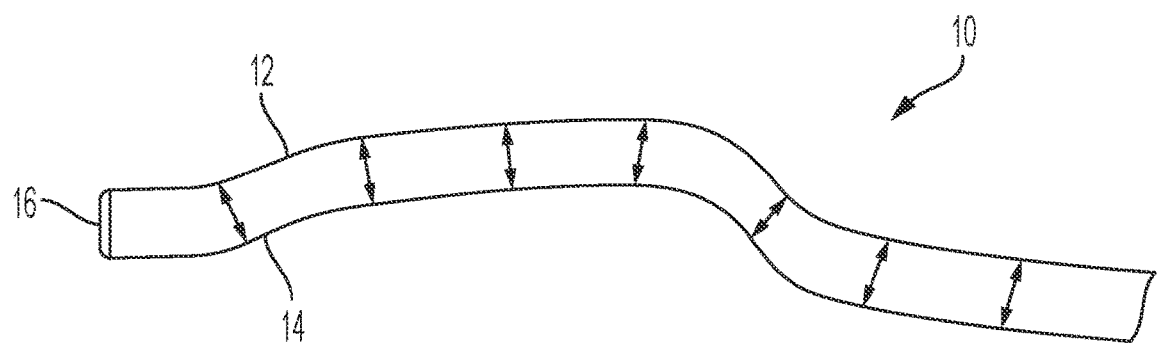
FIG. 6 is another view of a sensor strip formed from a sliding strip and a reference strip.

The multibend sensor 10 shown in FIG. 6 comprises a sliding strip 12 and a reference strip 14. Finding the shape of the reference strip 14 is the goal. At fixed intervals along the reference strip the corresponding shifted position along the sliding strip 12 is measured. By corresponding, it is meant that points that lie at the same angle with respect to the common center of the radius of curvature are used. Another way to say this is that if a normal to the curve of the reference strip 14 is constructed at the measurement point, a measurement will be made where it intersects the sliding strip 12.

Figure 7:
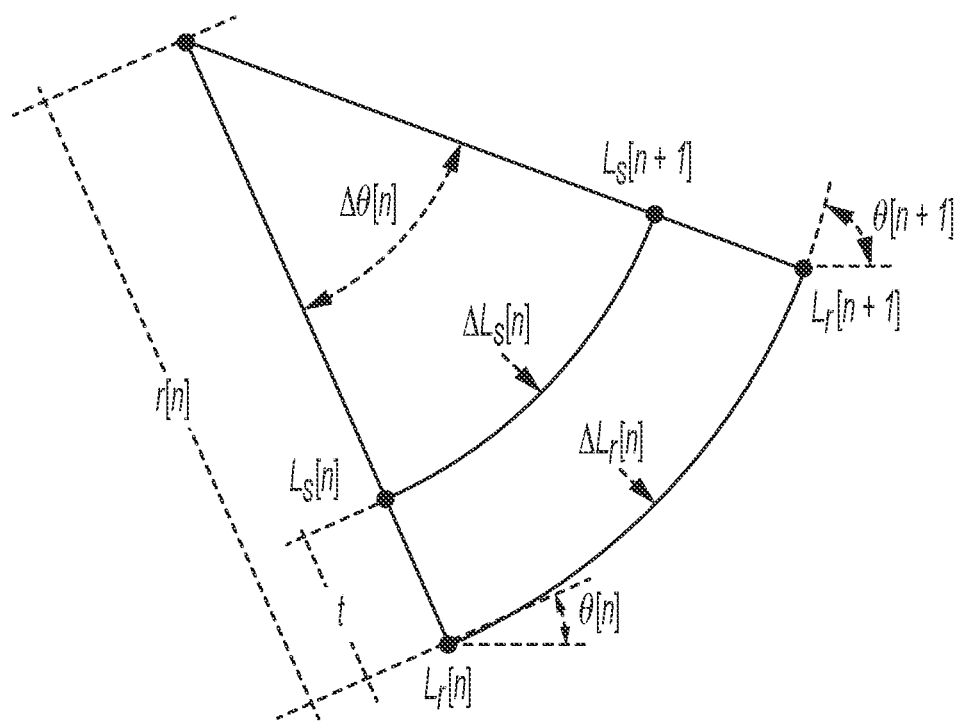
FIG. 7 is a diagram illustrating the calculations of a segment.

Referring now to FIG. 7, a single circular arc segment that spans from n to n+1 (segment n) on both the reference strip 14 and sliding strip 12 is provided as an example. Segment n is shaped into a circular arc of radius r[n] in a counterclockwise direction. Thus, the reference strip 14 has radius r[n] while the sliding strip is inside with a smaller radius of r[n]−t. Starting angle θ[n] is the tangent at the beginning of the arc. The ending angle is the tangent to the arc at its end, θ[n+1]. Similar to the calculation above, $L_r$[n] is the length of the reference strip 14 to measurement point n. $L_s$[n] is the length of the sliding strip 12 to measurement point n. On the side of the reference strip 14, the segment begins at $L_r$[n] and ends at $L_r$[n+1]. Similarly, the corresponding sliding strip 12 extends from $L_s$[n] to $L_s$[n+1]. The signed radius of curvature and the signed angular extent of the reference strip 14 segment can be found.

We define the length of the reference strip 14 in segment n as:

$$\Delta L_r[n] = L_r[n+1] - L_r[n]$$

and the length of the corresponding sliding strip as:

$$\Delta L_s[n] = L_s[n+1] - L_s[n]$$

Similarly, we define the total subtended angle of this segment as:

$$\Delta \theta[n] = \theta[n+1] - \theta[n]$$

For the case of positive curvature (r[n]>0 and Δθ[n]>0), the sliding strip 12 is shaped into a tighter curve than the reference strip 14. Thus, $\Delta L_s[n] < \Delta L_r[n]$, even though they subtend the same angle, Δθ[n]. Working in radians, the length of the reference segment is:

$$\Delta L_r[n] = r[n]\Delta\theta[n]$$

and the length of the corresponding sliding segment is:

$$\Delta L_s[n] = (r[n] - t)\Delta\theta[n]$$

Given the two lengths and the spacer thickness, we can solve for the radius of curvature of this segment:

$$r[n] = \frac{t\Delta L_s[n]}{\Delta L_r[n] - \Delta L_s[n]}$$

This same equation applies when the curve proceeds clockwise, giving a negative ending angle and negative radius of curvature. We can also solve for the subtended angle of the arc:

$$\Delta\theta[n] = \frac{\Delta L_r[n] - \Delta L_s[n]}{t}$$

A series of circular arcs of known length, angular extent, and radius of curvature is now known. This series can be pieced together to model the complete curve of the reference strip 14. It will be noted that, in an embodiment, multibend sensors have continuous flexure along their length and, thus, they are inherently continuous in their first derivative. Therefore, to maintain a continuous first derivative from segment to segment, the tangents of adjoining segments match. To put this another way, the ending angle of each segment matches the starting angle of the next segment.

Figure 8:
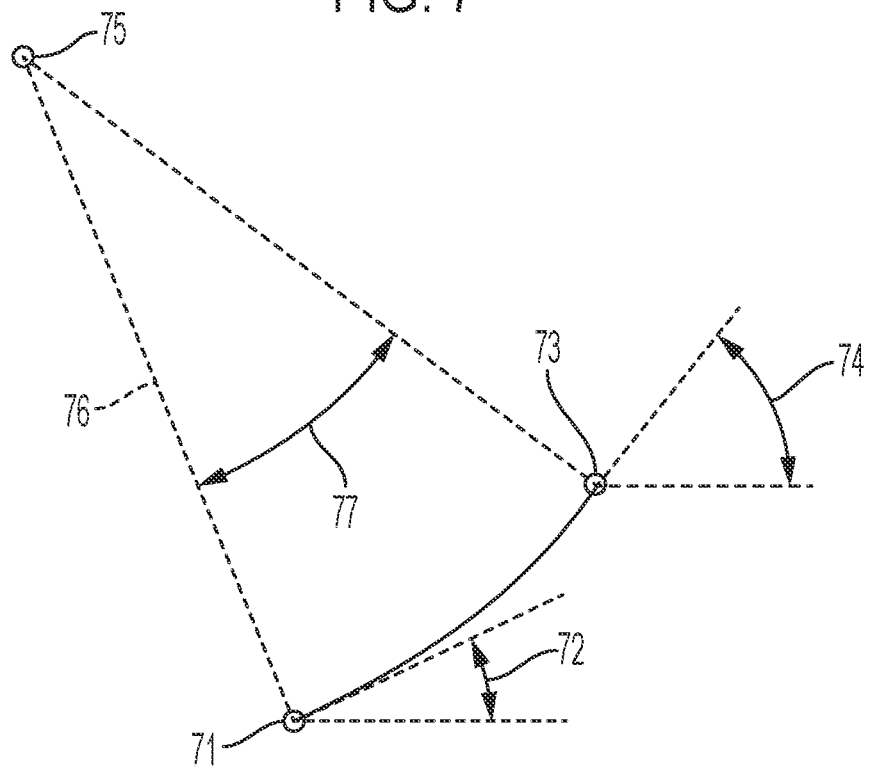
FIG. 8 is a diagram illustrating the calculations of a segment.

Consider a single arc as shown in FIG. 8. A starting angle 72, θ[n], and an ending angle 74, θ[n+1], which are tangent to the arc at its endpoints can be determined. It can be presumed that sequential segments connect smoothly—i.e. that the derivative is continuous at the point of connection. This is why the connection points are described by a single tangent angle.

The arc begins at a known starting point 71, (x[n], y[n]), and at an initial known angle 72 of θ[n] and proceeds to an unknown ending point 73, (x[n+1], y[n+1]), at an unknown ending angle 74 of θ[n+1].

The change in angle from starting point to the ending point is just the turning of the segment angle, Δθ[n]. To find the x, y translation, the increment in x and y over the arc is added to the previous point. For convenience, the center of the radius of curvature of the arc is considered to be at the origin and used to calculate endpoint positions. The difference in these is then applied to the known starting point.

For this calculation, the angles from the center that form the arc are known. The normal to θ[n] is $$\theta[n] - \frac{\pi}{2}.$$

For an arc of positive radius of curvature, this gives the angle pointing out from the center of the radius of curvature. If the radius of curvature is negative, it points in the opposite direction. This results in a sign flip that is corrected by using the signed radius of curvature. The endpoints can then be found iteratively via these equations:

$$x[n+1] = x[n] + r[n]\cos\left(\theta[n+1] - \frac{\pi}{2}\right) - r[n]\cos\left(\theta[n] - \frac{\pi}{2}\right)$$

$$y[n+1] = y[n] + r[n]\sin\left(\theta[n+1] - \frac{\pi}{2}\right) - r[n]\sin\left(\theta[n] - \frac{\pi}{2}\right)$$

These equations can be slightly simplified using trig identities.

$$x[n+1] = x[n] + r[n](\sin(\theta[n+1]) - \sin(\theta[n]))$$

$$y[n+1] = y[n] + r[n](\cos(\theta[n]) - \cos(\theta[n+1]))$$

These equations describe the series of circular arcs that model the bend. A circular arc is typically described by its center 75, ($C_x[n]$, $C_y[n]$), its radius of curvature 76, r[n], a starting angle, and an angular extent 77, $\theta_r[n]$.

The center of an arc segment can be found by starting at (x[n],y[n]), and following the radius to the arc center ($C_x[n]$, $C_y[n]$). The starting angle is found from the normal at the point (x[n],y[n]), which is $$\theta[n] - \frac{\pi}{2}.$$

The center is then:

$$C_x[n] = x[n] + r[n]\cos\left(\theta[n] - \frac{\pi}{2}\right) = x[n] + r[n]\sin(\theta[n])$$

$$C_y[n] = y[n] + r[n]\sin\left(\theta[n] - \frac{\pi}{2}\right) = y[n] - r[n]\cos(\theta[n])$$

Note that the use of the signed radius of curvature ensures following the normal to the center.

The starting angle is:

$$\left(\theta[n] - \frac{\pi}{2}\right)\text{sign}(r[n])$$

The sign is needed to flip the angle if the arc proceeds clockwise. The extent of the arc is $\theta_r[n]$, which is also a signed value.

Sensitivity to Measurement Error

Any real measurement of shift will be imperfect, making it important to understand how measurement errors impact the accuracy of the modelled curve. In jointed arms, noisy measurements of joint angles quickly accumulate, causing significant errors in the final position of the end effector. For instance, on multi-axis robot arms, position is usually determined via a series of encoders—one on each joint. High precision encoders are typically required because any errors in each joint measurement accumulate. For a planar arm, the angular error at the end of the arm is simply the sum of all the measurement errors in each joint. The location error of the endpoint is also wildly impacted by all of the joint errors-particularly the ones at the beginning of the arm.

Measurement errors in the multibend sensor are more forgiving. In an embodiment, error propagation is mitigated because measurement errors for each arc are not independent.

As an example, consider the case of a multibend sensor with two measurement points. The curvature of the first segment is found by determining the relative shift at the first measurement point. In this example, the measurement is corrupted by noise and an incorrectly low shift reading is recorded. The relative shift of the second segment is then found by taking the total shift at the second measurement point and subtracting off the shift from the first measurement point. The error at the first point will now cause a corresponding error in the second segment that is opposite in sign from the error in the first segment. Thus, the two segments will end up with curvature errors that tend to cancel each other out. In an embodiment, the error in final angle is completely unimpacted by the error at the first measurement point.

To show the sensitivity to error, we revisit the example of two successive segments. We define the starting point of the curve as:

$x[0]=0$ $y[0]=0$ $\theta[0]=0$

By definition, $\Delta L_r[0]=0$ and $L_s[0]=0$. We can now calculate the ending angle of segment 0:

$$\begin{aligned}\theta[1] &= \Delta\theta[0] + \theta[0] \\ &= \Delta\theta[0] \\ &= \frac{\Delta L_r[0] - \Delta L_s[0]}{t} \\ &= \frac{L_r[1] - L_s[1]}{t}\end{aligned}$$

Next, we find the ending angle of segment 1.

$$\begin{aligned}\theta[2] &= \Delta\theta[1] + \theta[1] \\ &= \frac{\Delta L_r[1] - \Delta L_s[1]}{t} + \frac{L_r[1] - L_s[1]}{t} \\ &= \frac{L_r[2] - L_s[2]}{t}\end{aligned}$$

As can be seen, the ending angle calculation has no dependence on any earlier measurements. This means that any errors in earlier measurements do not contribute error in the ending angle of each segment.

As will be noted by those skilled in the art, the above noted results prove advantageous over traditional solutions that build upon a series of angular encoders which have a practical limit on the number of encoders that can be strung together.

Physical Implementation

Figure 9:
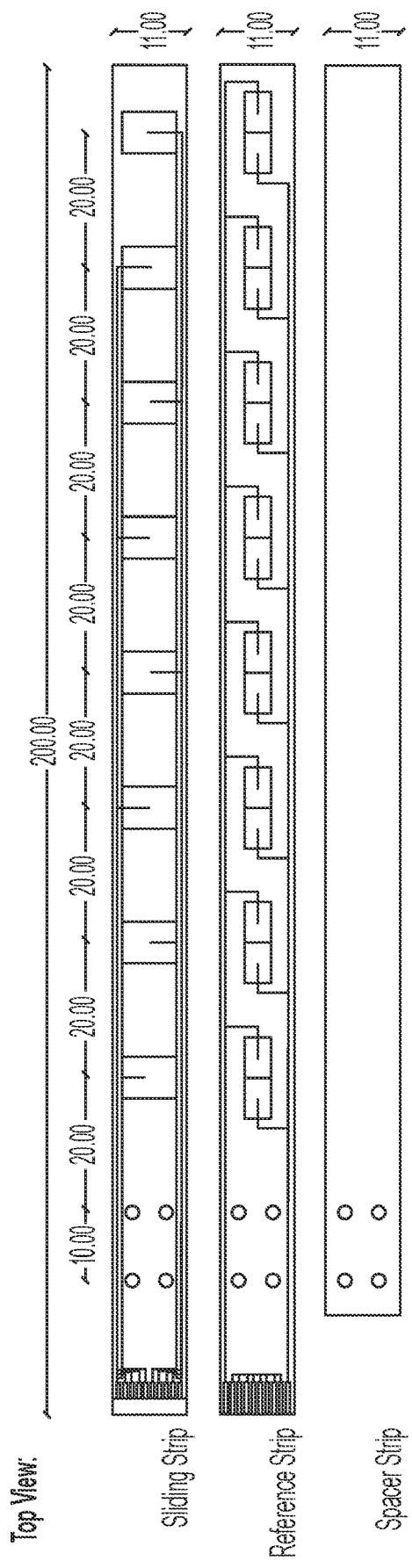
FIG. 9 shows a top view of a sliding strip, a reference strip, and a spacer strip of a multibend sensor.
Figure 10:
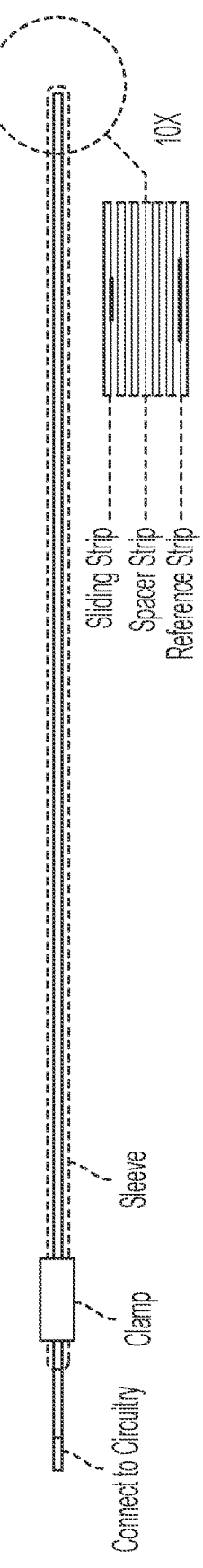
FIG. 10 shows a side view of the multibend sensor of FIG. 9.

Referring now to FIGS. 9 and 10, a reference strip and a sliding strip of a multibend sensor are provided. A plurality of transmit electrodes moves along a corresponding pattern of receive electrodes. In an embodiment, position is determined by examining the change in coupling capacitance between the transmit and receive electrodes. In an embodiment, a pattern of interdigitated electrodes allows one to perform differential measurements by comparing the capacitance of overlapping electrodes to determine relative shift. The differential nature of this measurement makes it highly insensitive to various types of error. In addition to the electrode pattern shown in FIG. 9, other electrode patterns can be implemented that will further provide measurements that can help determine the overall movement and shape of the multibend sensor.

In an embodiment, a plurality of the electrodes are adapted to transmit signals and a plurality of the electrodes are adapted to receive signals from the electrodes that are transmitting signals. In an embodiment, the electrodes adapted to transmit signals and the electrodes adapted to receive signals may be switched or alternated depending on the implementations. In an embodiment, an electrode adapted to transmit a signal may at a different time also be adapted to receive a signal. Received signals are used in order to determine movement of one strip with respect to the other strip. In an embodiment, electrodes can be patterned on standard flexible printed circuit boards (PCB) when creating the reference strip and the sliding strip. The capacitance through the spacer can be measured, and relative position determined.

In an embodiment, the transmit strip has a plurality of equally spaced electrodes which align with an equal number of differential electrode pairs on the receive strip. When the strips are flat, each transmit electrode will be centered over a receive pair such that the differential capacitance is zero. As the two strips shift relative to each other, the transmit pads will move out of alignment with the receive pads, unbalancing the differential capacitance. In an embodiment, the electrodes are arranged as to have significant overlap to minimize the impact of skew and fringing fields, giving a linear change in differential capacitance with respect to shift.

In an embodiment, the transmit and receive pads are kept at a fixed spacing by interposing a plurality of polyimide strips. In an embodiment, the amount of shift is proportional to the thickness of the spacing. In an embodiment, the thickness is 0.5 mm. In an embodiment, a single spacer is used. In an embodiment, a plurality of spacers are used to maintain accurate spacing while allowing the device to be pliable.

In an embodiment, the strips are held pressed together via an elastic sleeve, while still allowing them to shift against each other along the length. In an embodiment, a clamp passes through alignment holes on the strips to constrain motion on that end. In an embodiment, gold finger contacts allow the strips to be inserted into connectors on opposite sides of a controller board. In an embodiment, the strips are integrally manufactured with a controller board.

Figure 11:
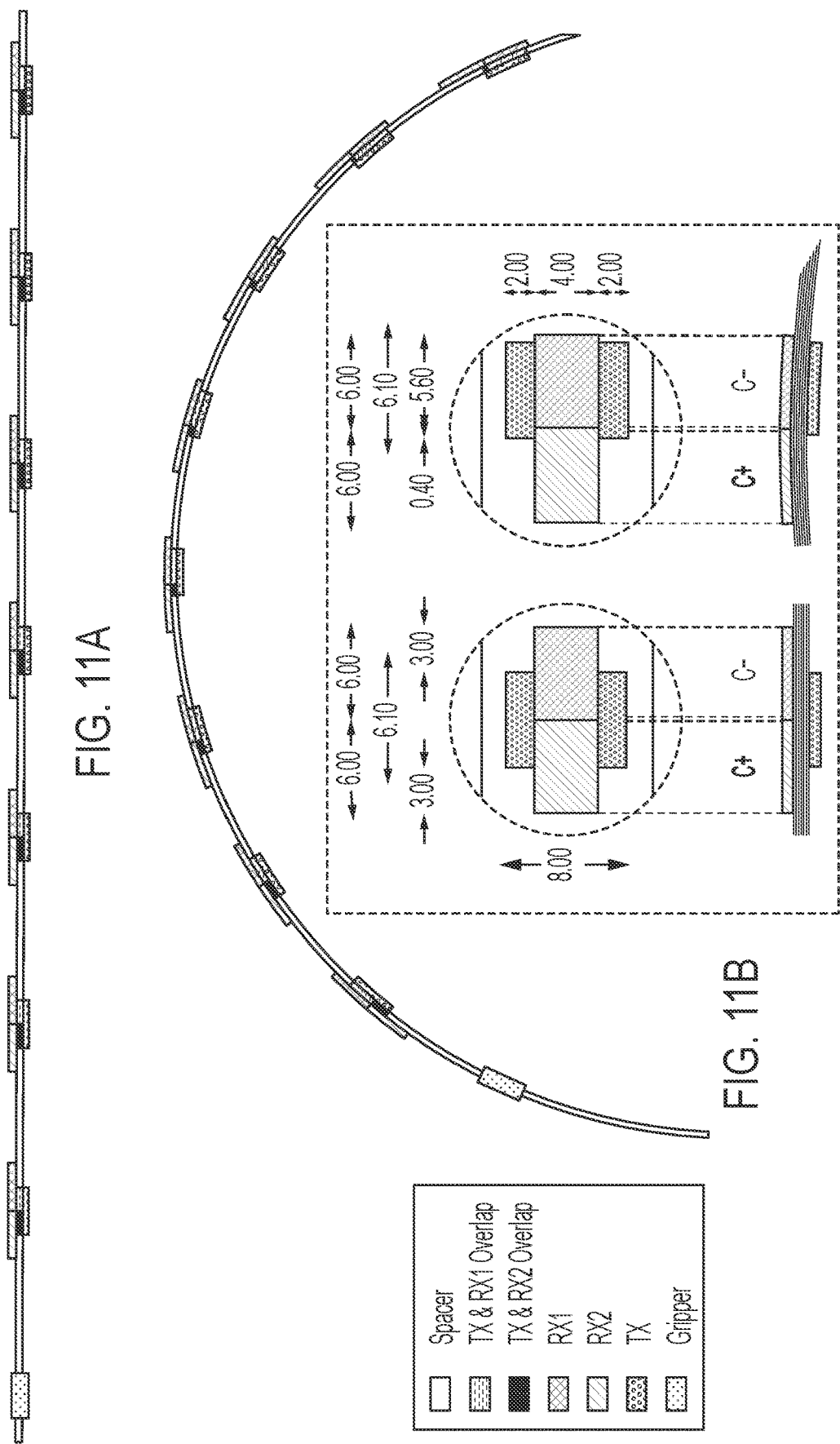
FIG. 11A illustrates a multibend sensor in a flat position.
FIG. 11B illustrates a multibend sensor in a bent position.
FIG. 11C illustrates representative electrode positions when a multibend sensor is in a flat position and in a bent position.

FIGS. 11A and 11B illustrate a multibend sensor in a flat position and a bent position, respectively. In an embodiment, the electrodes shift as the sensor is flexed. FIG. 11C illustrates the relationship between the relative shift and differential capacitance when the multibend sensor is in a flat position and in a bent position. In an embodiment, when the multibend sensor is in a flat position, the transmit electrodes are centered between two receive electrodes (i.e., no shift) and the differential capacitance is zero. In an embodiment, when the multibend sensor is bent in at least a portion of the sensor, at least one transmit electrode overlaps one receive electrode from the set of receive electrodes more than the other(s) receive electrode(s) (i.e., shift) creating a non-zero differential capacitance.

In an embodiment, a single channel, 24-bit differential capacitance to digital converter is used to perform the capacitance measurements. In an embodiment, using a series of ultra-low capacitance multiplexers, shift at 8 points along the strips can be successively measured. In an embodiment, the capacitances measured are sub-pico farad.

In an embodiment, when substantial parasitic capacitances due to the proximity of various traces is noted, a calibration procedure is used. First, the static impact of the parasitic capacitances are measured when the sensor is laid flat. Then, this value is subtracted off of later readings to find the differential capacitance due to the electrodes.

In an embodiment, the circuit can do a full sweep of the multibend sensor about 10 times per second, while drawing less than 100 mW.

Evaluation and Results

The performance characteristics of an embodiment of a multibend sensor were tested using a simple parallel plate model. A dielectric constant k of 3.5 for Polyimide was assumed and a sensitivity of 0.062 pF/mm of shift was calculated.

As shown in FIGS. 11A, 11B and 11C, in an embodiment, the transmit electrodes lay centered on the corresponding receive electrode pairs when the sensor is laid flat. As the sensor is bent, the receive and transmit pads misalign. As shown in FIG. 11C, in an embodiment, the shift can only go +/−3 mm before the transmit electrodes extends beyond the corresponding receive electrodes. In this embodiment, therefore, the maximum bend that the sensor can measure is limited. As we have shown, the shift at any point is only a function of the ending angle. For any segment n:

$$\theta[n] == \frac{L_r[n] - L_s[n]}{t}$$

In an embodiment, with a shift of +/−3 mm and a thickness of 0.5 mm, the maximum ending angle is 6 radians, or about 244 degrees. In an embodiment, the ending angle at any measurement point does not exceed 6 radians. In an embodiment, to ensure good linearity, the ending angle at any measurement point is less than 6 radians. It should be noted that in those embodiments, this constraint does not limit the number of bends. For example, if the sensor were formed into a sinusoid, the shift would cyclically rise and fall, returning to zero at the end of each cycle. (If the amplitude was high enough, the maximum ending angle could be exceeded at some points, but this is not dependent on the number of bends.) However, if the sensor is formed into a single circular arc as in FIG. 11B, the shift continues to linearly accumulate. So, in an embodiment, if the sensor is wrapped too tightly, it will exceed the allowable range.

In an embodiment, the performance of the device was tested using a number of circular arc test forms of known radii (from 40 mm to 600 mm) onto which the multibend sensor could be placed. The sensor was placed onto the test forms, data was collected, and the radius for each segment was calculated. The results are shown in Table 1 (below).

TABLE 1

| Measurement Results | | | | |
|---|---|---|---|---|
| Reference Radii(mm) | Constructed Radii (mm) | Error (%) | STD | CV |
| 40 | 40.23 | −0.58 | 0.22 | −0.39 |
| 50 | 49.85 | 0.29 | 0.10 | 0.35 |
| 60 | 60.82 | −1.37 | 0.15 | −0.12 |
| 70 | 70.76 | −1.07 | 0.03 | −0.03 |
| 80 | 79.01 | 1.25 | 0.13 | 0.11 |
| 90 | 89.90 | 0.15 | 0.30 | 1.97 |
| 100 | 99.08 | 1.11 | 0.55 | 0.49 |
| 125 | 126.16 | −0.02 | 0.27 | −0.23 |
| 150 | 147.43 | 1.80 | 0.42 | 0.24 |
| 175 | 175.35 | −0.17 | 0.18 | −1.03 |
| 200 | 201.58 | −0.60 | 0.35 | −0.59 |
| 300 | 285.03 | 4.98 | 0.73 | 0.15 |
| 400 | 380.83 | 4.79 | 0.56 | 0.12 |

TABLE 1-continued

| Measurement Results | | | | |
|---|---|---|---|---|
| Reference Radii(mm) | Constructed Radii (mm) | Error (%) | STD | CV |
| 500 | 404.60 | 19.07 | 1.04 | 0.05 |
| 600 | 453.69 | 24.38 | 0.46 | 0.02 |

In an embodiment, a multibend sensor accurately estimates the radii for the curves with radii below 200 mm. In an embodiment, a multibend sensor errors for curves with very large radii have little impact on the accuracy of the curve reconstruction.

Figure 12:
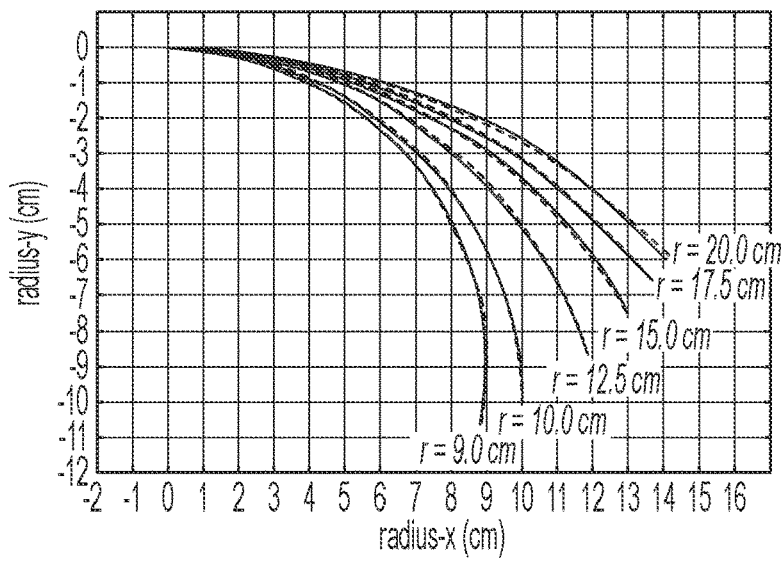
FIG. 12 illustrates example multibend sensor data from curves with known radii.

Referring now to FIG. 12, example curve reconstructions when the sensor is placed on forms with radii of curvature ranging from 90 mm to 200 mm along with their ideal curves is shown. As will be noted by those skilled in the art, in an embodiment, when a measured curve starts to drift off of the ideal, later segments help pull it back on.

Correcting Sources of Error

Figure 13:
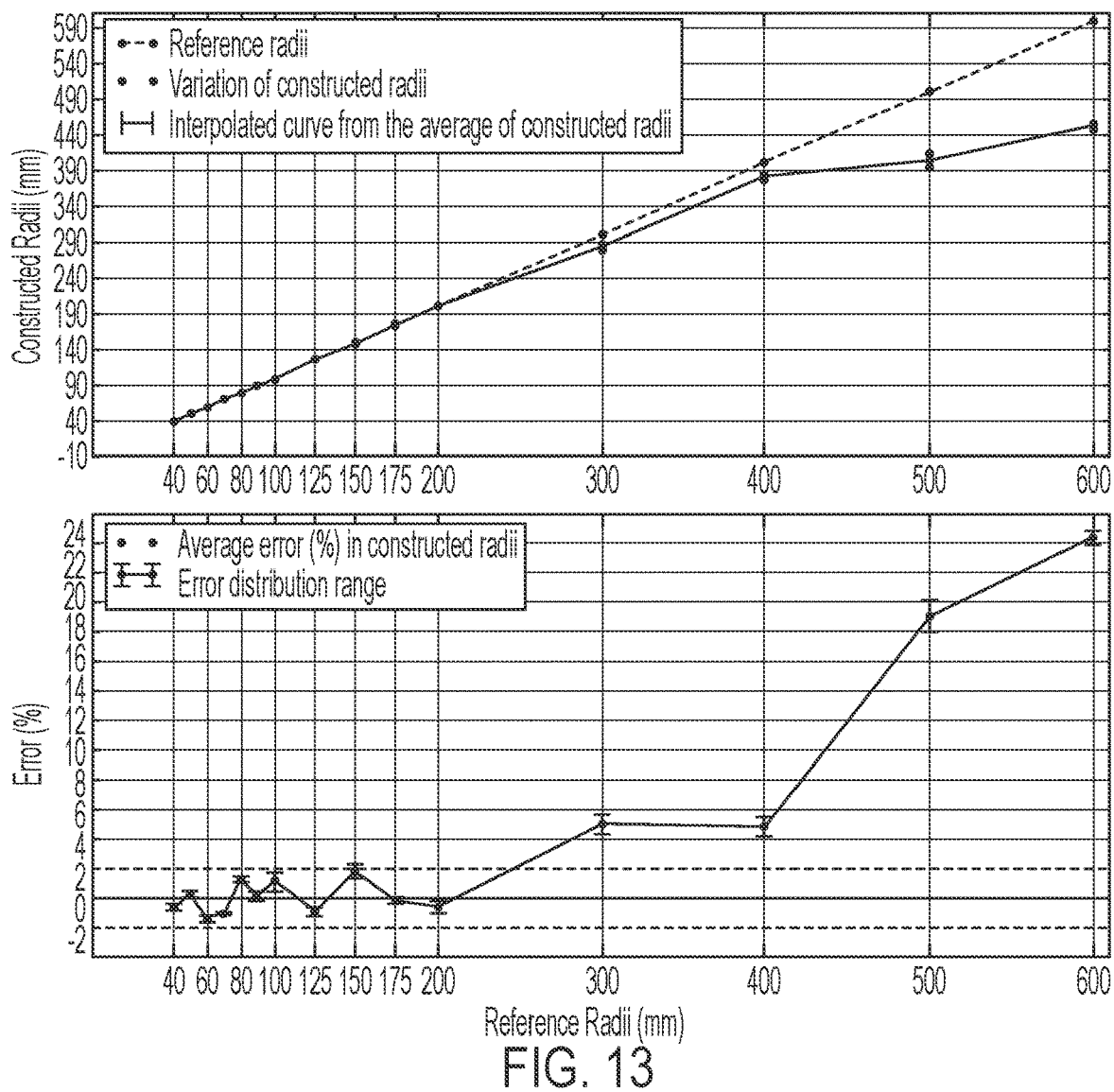
FIG. 13 illustrate testing results of a multibend sensor with a reference curve.

Referring now to FIG. 13, testing results of a multibend sensor with a reference curve are shown. The top graph of FIG. 13 shows a constructed v. reference radius. The solid line shows the interpolated curve of the average constructed (i.e., measured) radii. The dashed line shows the ideal characteristic curve. The dots show the variation in measured data. In an embodiment, the variation arises from random noise. The bottom graph of FIG. 13 shows measurement errors.

As noted above, in an embodiment, a capacitive sensing system may be susceptible to parasitic capacitances due to the asymmetric layout that cause a non-zero differential capacitance even when the transmit and receive electrodes are in a flat orientation. Also as noted above, since these are static, they can be measured in the flat position, and then subtracted off of all future measurements.

In an embodiment, material tolerance varies does not impact bend measurements. In an embodiment, sheet material is typically specified with a +/−5% thickness tolerance. In an embodiment, there may be small errors in the sizing of the electrodes and the gain of the converter. These factors may result in a change in the sensitivity and can be compensated for with a single constant. In an embodiment, iterative testing and calibrating cycles can be employed to determine the value of the constant to achieve an acceptable fit to a known curve.

In an embodiment, fringing fields may be a source of non-linearity, particularly when approaching the shift limit. However, this phenomenon can be characterized and compensated.

Applications and Interaction Techniques

In-Air Gesture Input Device

As noted above, a common application for resistive bend sensors has been finger tracking on glove input devices. Having only a measurement of gross flexure, these provided a crude estimate of finger position. Even that requires a model of finger structure and specific joint locations which vary dramatically among different users. Multibend sensors as described herein can overcome these limitations.

Figure 14:
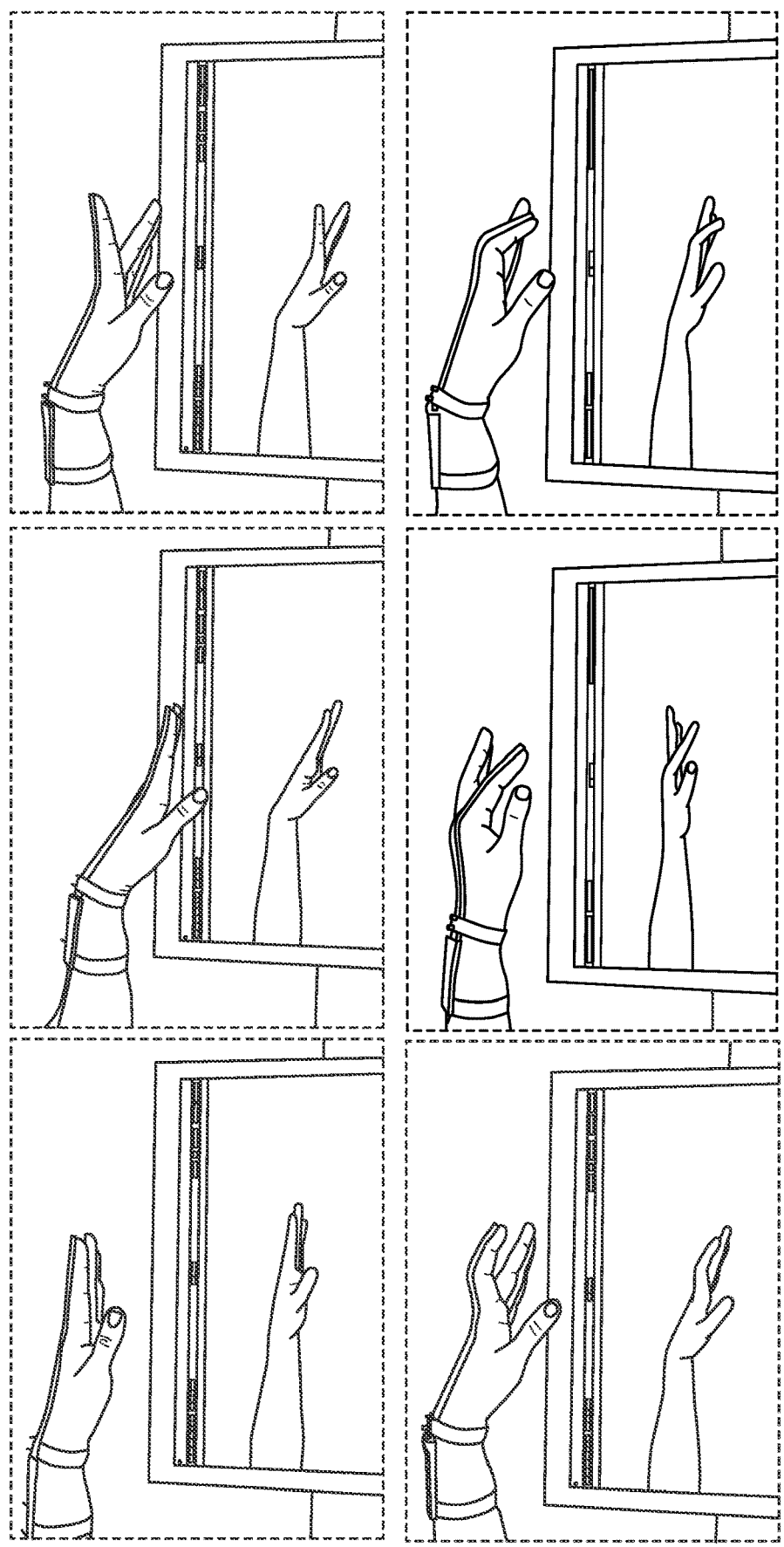
FIG. 14 illustrates a multibend sensor attached to a user's wrist and index fingers.

FIG. 14 illustrates a multibend sensor attached to a user's wrist and index finger, the resulting reconstructed hand models are shown in different poses. In an embodiment, the joint positions are updated in real-time. In an embodiment, a multibend sensor reports an 8-segment shape model over its length, which is adequate resolution for mapping the deformation data onto the wrist and finger joint positions.

This provides accurate and continuous motion tracking, enabling in-air gesture control of user interfaces for navigation, selection, hover, pressing, scrolling, etc.

In an embodiment, a multibend sensor with a thin thickness, about 1.0 mm, and proper width, about 11.0 mm, has a convenient size to be incorporated into the most general-size smart gloves. In an embodiment, reading the sensor data in 8 points on the length of about 20 cm, allows adequate resolution for mapping the deformation data into wrist and finger joints' positions for accurate and continuous motion tracking. In an embodiment, such properties allow developing an in-air gesture input device to control user interfaces by navigation, selection, hover, pressing, scrolling, etc. in a variety of use cases like gaming, music performance, virtual and augmented reality environments. In an embodiment, a multibend sensor is capable of tracking joints poses precisely, continuously and with low latency.

Posture Monitoring

In an embodiment, real time monitoring of human poses and tracking of skeletal movements is provided to adequately provide feedback to a user. In an embodiment, the feedback is provided in relation to health care requirements. In an embodiment, a multibend sensor is a low-cost, lightweight, easy-to-use, accurate sensor for long-term and regular wearable joint monitoring systems which helps detecting physical disabilities, rehabilitation processes, assessing athlete performance, In an embodiment, multibend sensors are used for many health applications where a detailed understanding of body motion is desired. In an embodiment, multibend sensors can easily be incorporated into patient wearable systems because of their precision, low-cost, low power, lightweight and slim in form factor.

Figure 15:
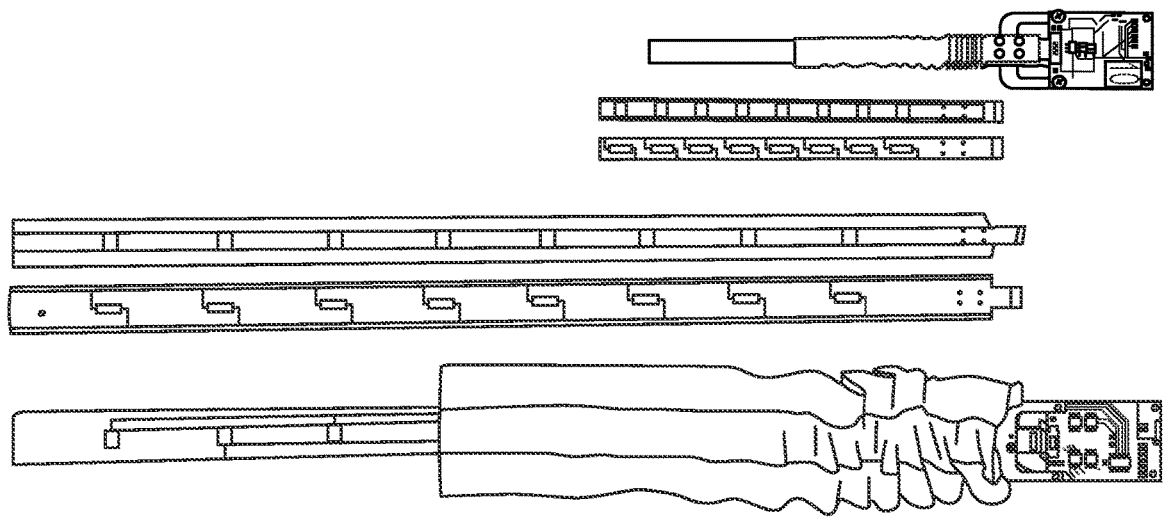
FIG. 15 illustrates multiple embodiments of a multibend sensor.

Referring now to FIG. 15, multiple embodiments of a multibend sensor are shown. In an embodiment, a multibend sensor is about half a meter long, 24 mm wide and about 1 mm thick. In an embodiment, the electrode patterns are the same as described herein, but spread out to cover the longer distance.

Figure 16:
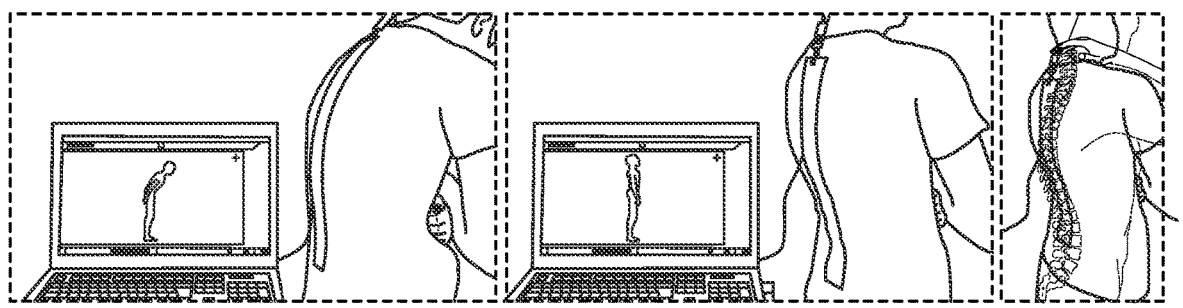
FIG. 16 illustrates an embodiment of a multibend sensor used to track spinal cord movements.

FIG. 16 illustrates an embodiment of a multibend sensor used to track spinal cord movements. In an embodiment, a multibend sensor is attached to a compression garment using Velcro strips so that it tracks the motion of the spine. In an embodiment, a multibend sensor used for skeletal tracking may comprise at least 8 segments. In an embodiment, a multibend sensor used for skeletal tracking may comprise less than 8 segments. In an embodiment, a multibend sensor is wireless without the need for bulky wires or tethers.

Angular Ruler

Figure 17:
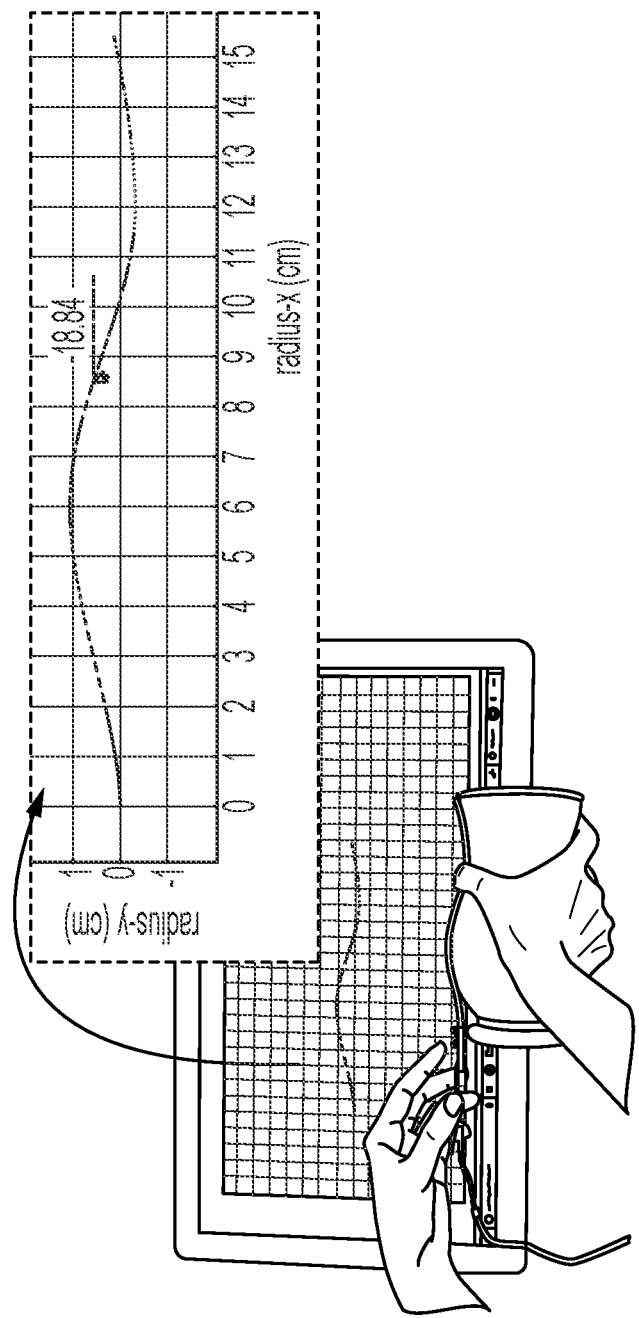
FIG. 17 illustrates a multibend sensor used as an angular ruler.

As will be noted by those skilled in the art, while it is easy to measure rectilinear objects, many aesthetically designed things feature free-form curves which are difficult to characterize. In an embodiment, a multibend sensor can act as a simple angular ruler which reports the precise shape of free-form geometries. FIG. 17 shows a multibend sensor used as angular ruler. In an embodiment, a multibend sensor can be used with an interactive user interface which allows collecting curve data in real-time. In an embodiment, a multibend sensor can be used with an interactive user interface that allows a user to click on any point along the curve and collect detailed information about the radii of the curvatures and the bend degree at that specific point.

As noted above, there are a variety of free-form objects without rectangular straight corners around us. Detecting such geometries allow better ways of user interactions with the surrounding environment. Multibend sensors as described herein can act as a low-cost, simple yet functional angular ruler which allows detecting the shape of such geometries.

In an embodiment, no materials with high flatness are used. In an embodiment, thin sheets with +/−5% thickness variation are used. In an embodiment, multibend sensor are not calibrated for thickness variations along the spacer strips. In an embodiment, multibend sensor are calibrated for thickness variations along the spacer strips.

It will be noted that while embodiments described herein use time division multiplexing (e.g., making each shift measurement serially in time) other techniques such as orthogonal frequency division can be used. Similarly, while embodiments described herein use capacitance measurements, resistance measurements may be used as well. In an embodiment, ratiometric capacitance measurements are used.

In embodiments that use time division multiplexing, a single curve may be constructed from data taken at different times. In an embodiment, data obtained using time division multiplexing is aligned in time. In an embodiment, multibend sensors use a circuit that does true simultaneous measurement at all points.

In an embodiment, electrode shielding techniques are used improve tolerance to handling and the proximity of nearby conductors.

In an embodiment, a multibend sensor can measure curves in multiple dimensions. In an embodiment, a multibend sensor measures bend in one plane. In an embodiment, a multibend sensor measures bend in multiple planes. In an embodiment, relative shift techniques described herein are used to characterize three-dimensional bends. In an embodiment, a multibend sensor can interpolate or fit a higher order function to model the change in curvature along the sensor, and thus create a model with effectively many more segments. In an embodiment, the underlying model of a segment is at least one of a circular arc and a different functional form.

An aspect of the present disclosure is a multibend sensor comprising a reference strip having a first plurality of electrodes, wherein each of the first plurality of electrodes is adapted to receive a signal; a sliding strip having a second plurality of electrodes, wherein each of the second plurality of electrodes is adapted to transmit at least one signal, wherein the sliding strip moves with respect to the reference strip; and measurement circuitry adapted to process signals received by the first plurality of electrodes, wherein the processed signals provide information regarding the relative position of the sliding strip to the reference strip.

Another aspect of the present disclosure is a multibend sensor comprising a plurality of reference strips having a first plurality of electrodes, wherein each of the first plurality of electrodes is adapted to receive a signal; a plurality of sliding strips having a second plurality of electrodes, wherein each of the second plurality of electrodes is adapted to transmit at least one signal, wherein at least one of the plurality of sliding strips moves with respect to at least one of the plurality reference strips; and measurement circuitry adapted to process signals received by the at least one of the first plurality of electrodes, wherein the processed signals provide information regarding the relative position of the sliding strip to the reference strip.

Yet another aspect of the present disclosure is a sensor for measuring a spinal bend comprising a housing adapted to conform to the shape of a spine, comprising a reference strip having a first plurality of electrodes, wherein each of the first plurality of electrodes is adapted to receive a signal; a sliding strip having a second plurality of electrodes, wherein each of the second plurality of electrodes is adapted to transmit at least one signal, wherein the sliding strip moves with respect to the reference strip; and measurement circuitry adapted to process signals received by the first plurality of electrodes, wherein the processed signals provide indication of movement of the sliding strip with respect to the reference strip, wherein the measured movement is related to spinal shape.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristic. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency-orthogonal to each other, in which case, they could not be the same frequency.

While the invention has been particularly shown and described with reference to a preferred embodiment thereof, it will be understood by those skilled in the art that various changes in form and details may be made therein without departing from the spirit and scope of the invention.

The invention claimed is:

1. A multibend sensor, comprising:
   a reference strip having a first plurality of electrodes, wherein each of the first plurality of electrodes is adapted to receive a signal;
   a sliding strip having a second plurality of electrodes, wherein each of the second plurality of electrodes is adapted to transmit at least one signal, wherein the sliding strip moves with respect to the reference strip, wherein an end portion of the reference strip and an end portion of the sliding strip are secured together by a common end portion, wherein the common end portion effects the movement of the sliding strip with respect to the reference strip; and
   measurement circuitry adapted to process signals received by the first plurality of electrodes, wherein the processed signals provide information regarding the relative position of the sliding strip to the reference strip.

2. The multibend sensor of claim 1, wherein the measurement circuitry processes the signals to determine a capacitance.

3. The multibend sensor of claim 1, wherein the measurement circuitry processes the signals to determine a resistance.

4. The multibend sensor of claim 1, wherein the reference strip and the sliding strip are secured to each other at one end.

5. The multibend sensor of claim 1, wherein the reference strip and the sliding strip are secured to each other at one end.

6. The multibend sensor of claim 1, wherein at least two of the first plurality of electrodes receive a signal from a corresponding electrode of the second plurality of electrodes.

7. A multibend sensor, comprising:
   a plurality of reference strips having a first plurality of electrodes, wherein each of the first plurality of electrodes is adapted to receive a signal;
   a plurality of sliding strips having a second plurality of electrodes, wherein each of the second plurality of electrodes is adapted to transmit at least one signal, wherein at least one of the plurality of sliding strips moves with respect to at least one of the plurality reference strips, wherein an end portion of the reference strip and an end portion of the sliding strip are secured together by a common end portion, wherein the common end portion effects the movement of the sliding strip with respect to the reference strip; and
   measurement circuitry adapted to process signals received by the at least one of the first plurality of electrodes, wherein the processed signals provide information regarding the relative position of the sliding strip to the reference strip.

8. The multibend sensor of claim 7, wherein the measurement circuitry processes the signals to determine a capacitance.

9. The multibend sensor of claim 7, wherein the measurement circuitry processes the signals to determine a resistance.

10. The multibend sensor of claim 7, wherein the information provided by the processed signals describes at least one curve in one plane.

11. The multibend sensor of claim 7, wherein the information provided by the processed signals describes at least one curve in a plurality of planes.

12. A sensor for measuring a spinal bend, comprising:
    a housing adapted to conform to the shape of a spine, comprising:
    a reference strip having a first plurality of electrodes, wherein each of the first plurality of electrodes is adapted to receive a signal;
    a sliding strip having a second plurality of electrodes, wherein each of the second plurality of electrodes is adapted to transmit at least one signal, wherein the sliding strip moves with respect to the reference strip, wherein an end portion of the reference strip and an end portion of the sliding strip are secured together by a common end portion, wherein the common end portion effects the movement of the sliding strip with respect to the reference strip; and
    measurement circuitry adapted to process signals received by the first plurality of electrodes, wherein the processed signals provide indication of movement of the sliding strip with respect to the reference strip, wherein the measured movement is related to spinal shape.

13. The sensor of claim 12, wherein the measurement circuitry processes the signals to determine a capacitance.

14. The sensor of claim 12, wherein the measurement circuitry processes the signals to determine a resistance.

15. The sensor of claim 12, wherein the measured movement is in one direction.

16. The sensor of claim 12, wherein the measured movement is in a plurality of directions.

* * * * *